United States Patent

Miyano et al.

[11] Patent Number: 5,596,666
[45] Date of Patent: Jan. 21, 1997

[54] ILLUMINATION SYSTEM FOR ENDOSCOPES

[75] Inventors: Hitoshi Miyano; Masaaki Morizumi, both of Omiya, Japan

[73] Assignee: Fuji Photo Optical Co., Ltd., Saitama-ken, Japan

[21] Appl. No.: 545,099

[22] Filed: Oct. 19, 1995

[30] Foreign Application Priority Data

Oct. 20, 1994 [JP] Japan ..................................... 6-254890

[51] Int. Cl.$^6$ ...................................................... G02B 6/06
[52] U.S. Cl. ............................................................. 385/118
[58] Field of Search ..................................... 385/115, 117, 385/118, 122, 147; 359/36, 40, 615

[56] References Cited

U.S. PATENT DOCUMENTS

| | | | |
|---|---|---|---|
| 4,831,437 | 5/1989 | Nishioka et al. | 348/71 |
| 4,878,112 | 10/1989 | Ieoka | 348/70 |
| 4,882,619 | 11/1989 | Hasegawa et al. | 359/615 |
| 4,902,115 | 2/1990 | Takahashi | 359/36 |
| 5,014,121 | 5/1991 | Tsujiuchi et al. | 382/255 |
| 5,148,502 | 9/1992 | Tsujiuchi et al. | 382/255 |
| 5,434,669 | 7/1995 | Tabata et al. | 356/345 |

*Primary Examiner*—Akm E. Ullah
*Attorney, Agent, or Firm*—Young & Thompson

[57] ABSTRACT

An endoscope illumination system having an objective lens system forming an image of an object of an internal organ or in a hollow structural body and a light guide fiber bundle for guiding illumination light generated by the light guide source to a light exit end thereof and illuminating the object includes a shift mechanism means for causing parallel movement of the optical axis of the light exit end with respect to and in a plane including the optical axis of the illumination lens system.

8 Claims, 3 Drawing Sheets

5,596,666

ILLUMINATION SYSTEM FOR ENDOSCOPES

BACKGROUND OF THE INVENTION

1. Field of the invention

The resent invention relates to an illumination system for endoscopes for medical and industrial use.

2. Description of Related Art

Endoscopes for use with external light sources are typically provided with at least one light guide fiber bundle for guiding light from the external light source to an distal end of the endoscope and illuminating an object in an internal organ or in the interior of hollow structural body. The distribution of illumination light provided by such a light guide fiber bundle does not always cover a view field of the endoscope which has a wide angle of view. In order for the endoscope to cover a wide angle of view field, diverging lens systems are incorporated so as to provide an appropriate distribution of illumination light. By using a concave lens system or a convex lens system as such a diverging lens system light beams from the light guide fiber bundle diverges to illuminate a wide angle of view field.

While the use of these diverging lens system provides illumination for a wide angle of view field, nevertheless, because the illumination system is relatively stationary with respect to an objective lens system, it can not change the distribution of illumination according to angles of sight. For example, in the case where a pair of illumination systems Si are disposed symmetrically with respect to and on diametrically opposite sides of an objective lens system So as shown in FIG. 5A, the illumination systems provides the distribution of illumination as shown in FIG. 5B. In this instance, an object at a relatively short distance is less illuminated at the center area of the view field of the objective lens system So as compared with in the peripheral area far from the optical axis of the objective lens system. Consequently, the distribution of illumination is not uniform over the view field of the objective lens system, providing an image having low brightness at the center area. In the case where a single illumination system Si is disposed on one side of an objective lens system So, the illumination system provides the distribution of illumination as shown in FIG. 6. In this instance, an object at an angle with respect to the optical axis of an objective lens system So is, on one hand, sufficiently illuminated at a relatively short distance and, on the other hand, less illuminated at a relatively long distance. As a result, an image of the object has a low brightness at one side thereof.

SUMMARY OF THE INVENTION

It is an object of the present invention to provide an illumination system for an endoscope which can provide a uniform distribution of illumination light over a view field of an objective lend system and enables the objective lend system to form an image of an object in spite of object positions.

The above object of the present invention is achieved by providing an endoscope illumination system having an objective lens system stationarily disposed in the distal end cap for forming an image of an object of an internal organ or in a hollow structural body and at least one light guide fiber bundle for causing illumination light generated by the light guide source to a light exit end thereof disposed in an distal end of the endoscope and illuminating said object. The illumination optical system includes an illumination lens system disposed in front of the light exit end of the light guide fiber bundle in the distal end cap so as to place its optical axis stationary relative to an optical axis of the objective lens system and diverging and directing illumination light beams toward a view field of the objective lens system and a shift means disposed in the distal end cap and linked with an distal end portion of the light guide fiber bundle for causing parallel movement of the optical axis of the light exit end with respect to and in a plane including the optical axis of the illumination lens system.

The shift means may comprise any one of a mechanical shift mechanism including a link mechanism, a magnetic shift mechanism including a magnet and an electrical shift mechanism including a piezo-electric element.

With the endoscope illumination system of the present invention, the field of illumination is changed according to object positions by causing parallel movement of the optical axis of the light exit end of the light guide fiber bundle relative to and in a plane including the optical axis of the illumination lens system, a uniform and sufficient distribution of illumination light is provided over the view field of the objective lens system in spite of object positions.

BRIEF DESCRIPTION OF THE DRAWINGS

The above and other objects and features of the present invention will be clearly understood from the following description with respect to a preferred embodiment thereof when considered in conjunction with the accompanying drawings, in which.

DETAILED DESCRIPTION OF THE PREFERRED EMBODIMENTS

Figure 1:
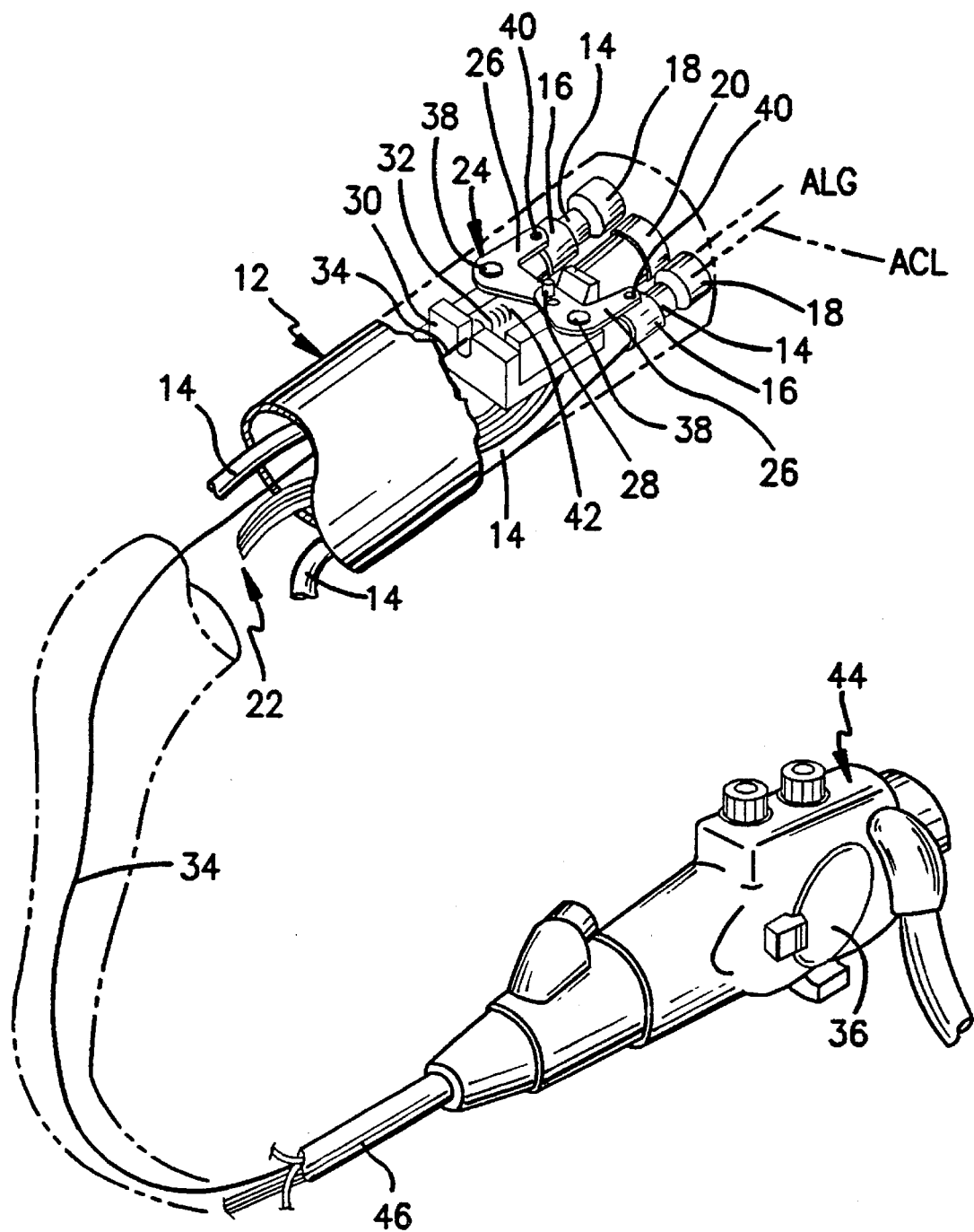
FIG. 1 is a perspective view partly in broken of an endoscope incorporating an illumination system in accordance with a preferred embodiment of the present invention.
Figure 2:
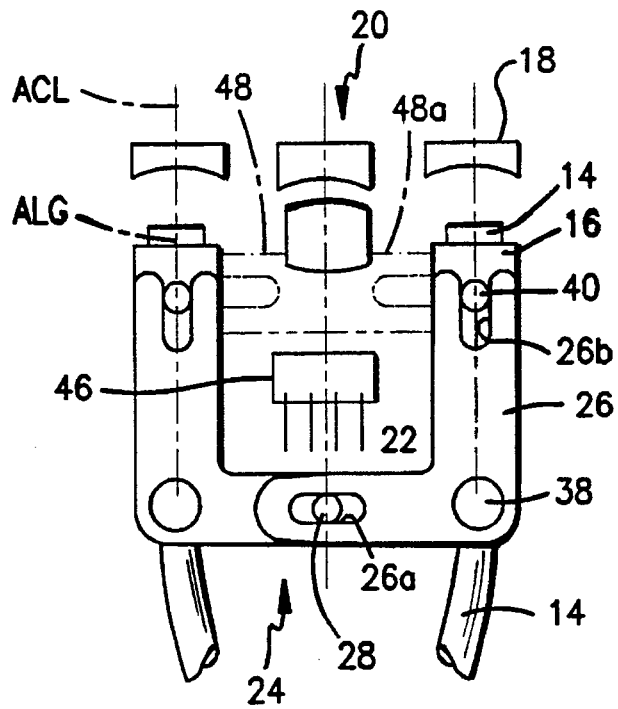
FIG. 2 is a plan view of a shift mechanism of the illumination system of the endoscope shown in FIG. 1.

Referring to the drawings in detail, in particular, to FIGS. 1 and 2 showing an endoscope illumination system in accordance with a preferred embodiment of the present invention, an endoscope typically has an operating handle 44 and a cylindrical distal end cap 12 connected by a flexible tube 46. A pair of light guide fiber bundles 14, each of which comprises an enormous number of optical fibers, extend in the flexible tube 46 between the cylindrical distal end cap 12 and an external light source (not shown) via the operating handle 44. Typically, the light guide fiber bundles 14 branches off from a single fiber bundle whose end is connected to the external light source so as to guide light generated by the light source to light exit ends of the respective light guide fiber bundles 14. The distal ends of the light guide fiber bundle 14 are held by cylindrical protection pipes 16 and separated at a predetermined distance. Within the distal end cap 12 there are incorporated illumination lens systems 18 comprising, for instance a concave lens for diverging light beams, in front of light exit ends of the light guide fiber bundles 14, respectively and are stationary relative to the distal end cap 12. Within the cylindrical distal end cap 12, there is installed an objective lens system 20 at the center between the light guide fiber bundle 14 which is stationary relative to the distal end cap 12. This objective lens system 20 forms an optical image on a photodetector device 20, such as a charge coupled device (CCD), positioned in a focal plane of the objective lens system 20. The photodetector device 46 generates video signals representative of an optical image formed thereon. The video signals are transmitted to an external TV receiver through wires 22. In place of the imaging system comprising the photodetector deice 46 and a TV receiver (not shown), an image guide fiber bundle and an eye piece may be used for direct observation.

Within the cylindrical distal end cap 12, there is further incorporated an optical axis shift mechanism 24 for causing parallel movement of an optical axis $A_{LG}$ of each light guide fiber bundle 14 relative to the optical axis $A_{CL}$ of the related illumination lens system 18 in a plane perpendicular to the optical axis $A_{CL}$ of the illumination lens system 18. The optical axis shift mechanism 24 comprises a supporting frame 30 secured to the cylindrical distal end cap 12 and a pair of L-shaped levers 26 mounted on the supporting frame 30 so as to turn around pivot pins 38 at their angles, respectively. These L-shaped levers 26 are operationally coupled at their arm ends by means of a coupling pin 28 secured to one of the L-shaped levers 26 and a guide slot 26a formed in another of the L-shaped levers 26. A stem of each L-shaped lever 26, which extends along the distal portion of the light guide fiber bundle 14, is formed at its free end with an open ended guide slot 26b in which a coupling pin 40 secured to the cylindrical protection pipe 16 is received for slide movement. The coupling pin 28 is linked with an externally operated shift knob 36 on the operating handle 44 by means of a wire 34 extending in the flexible tube 46. The wire 36 is provided near an end thereof with an abutment 42. Between the supporting frame 30, in particular an upright flange of the supporting frame 30, and the abutment 42 there is disposed a return spring 32 for urging the wire 36 in a direction in which the wire forces the L-shaped levers 26 toward their original positions where the optical axes $A_{LG}$ Of the light guide fiber bundles 14 are in alignment with the optical axes $A_{CL}$ of the related illumination lens systems 18, respectively, and positioned symmetrically with respect to the optical axis of the objective lens system 20. In order to guide the parallel movement of the cylindrical protection pipes 16 on which the coupling pins 40 are secured, respectively, a guide plate 48 is provided in the cylindrical distal end cap 12. The guide plate 48 is formed at opposite ends with guide slots 48a extending perpendicularly to the guide slots 26b of the L-shaped levers 26 and receiving therein the coupling pins 40, respectively, for slide movement.

With the optical axis shift mechanism 24 thus structured, when the shift knob 36 is turned against the return spring 32 in a direction where the wire 34 is pulled along the length of the flexible tube 46, the L-shaped levers 26 are caused to turn in opposite directions so as to shift the stem ends close to each other, causing parallel movement of the distal ends, and hence the optical axes $A_{LG}$, of the light guide fiber bundles 14. As a result, the optical axes $A_{LG}$ of the light guide fiber bundles 14 are shifted from the optical axes $A_{CL}$ of the related optical systems 18, respectively and approach to each other. This parallel movement of the optical axes $A_{LG}$ of the light guide fiber bundles 14 is symmetrical with respect to the optical axis of the objective lens system 20. When the shift knob 36 is freed, the return spring 32 is allowed to expand and forces the L-shaped levers 26 to their original positions, bringing the optical axes $A_{LG}$ of the light guide fiber bundles 14 in alignment with the optical axes $A_{CL}$ of the illumination lens systems 18, respectively.

Figure 3A:
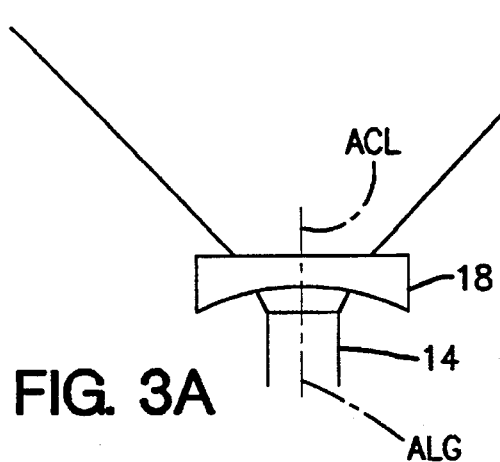
FIGS. 3A and 3B are illustrations showing optical operation of the illumination system using a concave lens system.
Figure 4A:
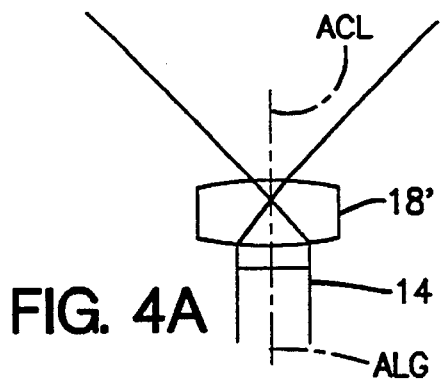
FIGS. 4A and 4B are illustrations showing optical operation of the illumination system using a convex lens system.
Figure 5A:
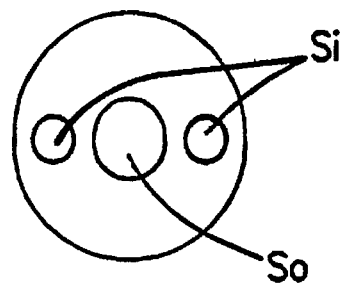
FIG. 5A is a schematic front view of a distal end of a prior endoscope.
Figure 5B:
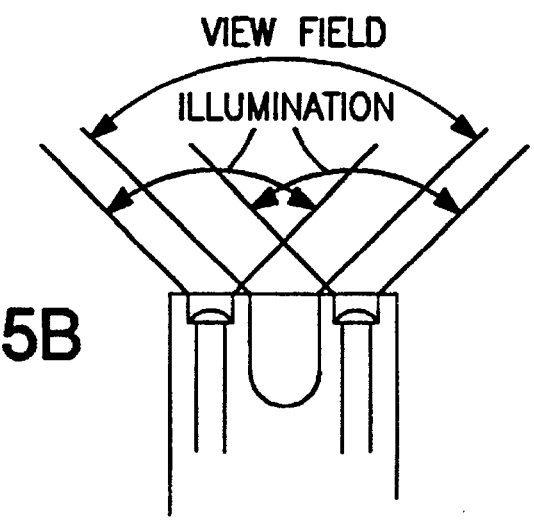
FIG. 5B is an illustration showing optical operation of the prior art endoscope of FIG. 5A.
Figure 6:
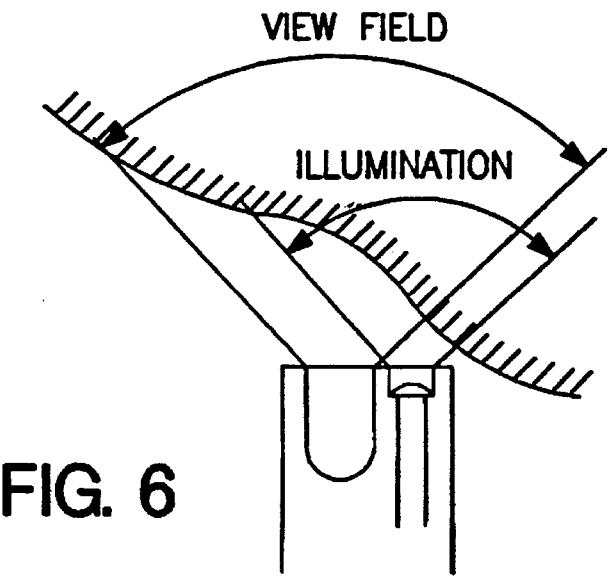
FIG. 6 is an illustration showing optical operation of still another prior art endoscope.

When the shift knob 36 is freed, the light guide fiber bundles 14 are in their original positions where the optical axes $A_{LG}$ are in alignment with the optical axes $A_{CL}$ of the related illumination lens systems 18, respectively. In the original position, each illumination lens system 18 diverges light beams from the light guide fiber bundle 14 symmetrically relative to its optical axis $A_{CL}$ as shown in FIG. 3A. Accordingly, the diverged light beams provide a wide angle of illuminated field within an internal organ as shown in FIG. 5B. In this instance, the distribution of illumination light provided by the illumination lens systems 18 is suitable for a surface of the internal organ at a relatively long distance from the objective lens system 20.

Figure 3B:
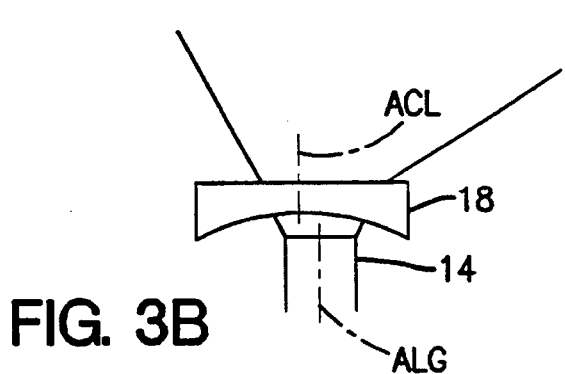
Figure 4B:
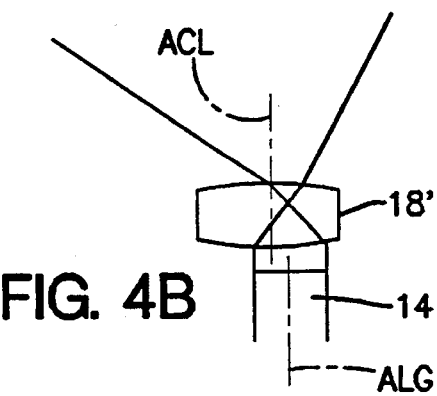

On the other hand, when the-shift knob 36 is turned against the return spring 32 so as to cause parallel movement of the optical axes $A_{LG}$ of the light guide fiber bundles 14 to shift them apart from the optical axes $C_{CL}$ of the related optical systems 18, respectively and approach to each other, each illumination lens system 18 provides a distribution of diverged light beams lope-sided toward the axis of the objective lens system 20. In other words, light beams passing through near the periphery of the illumination lens system 18 shifted from the optical axis $A_{LG}$ of the light guide fiber bundle 14 are refracted strongly toward the axis of the objective lens system 20 as shown in FIG. 3B as compared when the optical axis $A_{LG}$ of the light guide fiber bundle 14 is in alignment with the optical axis $A_{CL}$ of the illumination optical system 18 as shown in FIG. 3A. Together, light beams passing through near the center of the illumination lens system 18 shifted from the optical axis $A_{LG}$ of the light guide fiber bundle 14 are refracted weakly apart from the axis of the objective lens system 20 as shown in FIG. 3B as compared when the optical axis $A_{LG}$ of the light guide fiber bundle 14 is in alignment with the optical axis $A_{CL}$ of the illumination optical system 18 as shown in FIG. 3A. As a result, the diverged light beams provide a relatively narrow angle of illuminated field within an internal organ. This distribution pattern of illumination light provided by the illumination lens systems 18 is suitable for a surface of the internal organ at a relatively short distance from the objective lens system 20.

As apparent from the above description, in spite of operated angles of the shift knob 36, the center of illuminated field provided by the illumination lens systems 18 is made in alignment with the center of view field of the objective lens system 20, producing a clear image of an object at any position and any angle relative to the axis of the objective lens system 20 over the view field.

The illumination system may incorporate a convex illumination lens system 18'in place of the concave illumination lens system 18. In this instance, the shift mechanism must shift the light guide fiber bundle 14 in opposite direction to the direction in which illumination light beams is required to cause parallel movement.

It is to be understood that although the present invention has been described in connection with an endoscope with a pair of illumination guide fiber bundles disposed symmetrically relative to the optical axis of the objective lens system, the present invention is embodied in endoscope with one or more than two illumination guide fiber bundles disposed symmetrically relative to the optical axis of the objective lens system with the same results.

It is also to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. An illumination system for an endoscope having at least one light guide fiber bundle extending from an external light source into a distal end cap of said endoscope for guiding light generated by said light guide source to a light exit end thereof and an objective lens system stationarily disposed in said distal end cap for forming an image of an illuminated object of an internal organ, said illumination optical system comprising:

an illumination lens system disposed in front of said light exit end of said light guide fiber bundle in said distal end cap, said illumination lens system having an optical axis which is stationary relative to an optical axis of said objective lens system and diverging and directing illumination light beams from said light exit end of said light guide fiber bundle toward a field of view of said objective lens system;

shift means disposed in said distal end cap and linked with an distal end portion of said light guide fiber bundle for causing parallel movement of an optical axis of said light exit end of said light guide fiber bundle with respect to and in a plane including said optical axis of said illumination lens system; and an externally operated shift knob operationally linked with said shift means for causing said shift means to cause said parallel movement of said optical axis of said light exit end of said light guide fiber bundle relative to said axis of said objective lens system.

2. An illumination system as defined in claim 1, wherein said shift means comprises a mechanical shift mechanism including a link mechanism.

3. An illumination system as defined in claim 1, wherein said shift means comprises an magnetic shift mechanism including a magnet.

4. An illumination system as defined in claim 1, wherein said shift means comprises an electrical shift mechanism including a piezo-electric element.

5. An illumination system as defined in claim 1, wherein said shift means comprises a motion transforming mechanism operationally coupled between said light exit end of said light guide fiber bundle and said externally operated shift knob for transforming rotational motion of said externally operated shift knob into said parallel movement of said light exit end of said light guide fiber bundle.

6. An illumination system as defined in claim 5, wherein said motion transforming mechanism comprising an L-shaped lever mounted for pivotal movement on said distal end cap at an angle thereof, operationally coupled at one end to said light exit end of said light guide fiber bundle and at another end to said externally operated shift knob through a wire.

7. An illumination system as defined in claim 6, wherein said motion transforming mechanism further comprises a return spring disposed between said externally operated shift knob and said L-shaped lever so as to cause pivotal movement of said L-shaped lever in a direction in which said L-shaped lever cause parallel movement of said optical axis of said light exit end of said light guide fiber bundle toward said axis of said illumination lens system when said externally operated shift knob is free.

8. An illumination system as defined in claim 1, wherein said illumination lens system and said shift means are incorporated in association with each of two said light guide fiber bundles whose light exit ends are disposed and shifted symmetrically with respect to said optical axis of said objective lens system.

* * * * *